US007368106B2

(12) United States Patent
Murphy et al.

(10) Patent No.: US 7,368,106 B2
(45) Date of Patent: May 6, 2008

(54) USE OF A PROMOTER OF T-CELL EXPANSION AND AN INDUCER OF CD40 STIMULATION IN THE TREATMENT OR PREVENTION OF A PATHOLOGIC STATE

(75) Inventors: William J. Murphy, Reno, NV (US); Robert Wiltrout, Woodsboro, MD (US); Bruce Blazar, Golden Valley, MN (US); Susan Wilson, Alameda, CA (US)

(73) Assignees: The United States of America as represented by the Department of Health and Human Services, Washington, DC (US); University of Minnesota, Minneapolis, MN (US); Chiron Corporation, Emeryville, CA (US)

( * ) Notice: Subject to any disclaimer, the term of this patent is extended or adjusted under 35 U.S.C. 154(b) by 0 days.

(21) Appl. No.: 11/608,873

(22) Filed: Dec. 11, 2006

(65) Prior Publication Data
US 2007/0231299 A1 Oct. 4, 2007

Related U.S. Application Data

(62) Division of application No. 10/226,959, filed on Aug. 23, 2002, now Pat. No. 7,175,838.

(60) Provisional application No. 60/314,342, filed on Aug. 23, 2001.

(51) Int. Cl.
*A61K 39/395* (2006.01)
*A61K 38/20* (2006.01)
(52) U.S. Cl. ............... 424/85.2; 424/141.1; 424/143.1; 424/130.1; 514/2; 514/8; 514/12
(58) Field of Classification Search ..................... None
See application file for complete search history.

(56) References Cited

U.S. PATENT DOCUMENTS

| 5,843,648 A | 12/1998 | Robbins et al. |
| 6,045,788 A | 4/2000 | Smith |
| 6,106,823 A | 8/2000 | Vieira et al. |

FOREIGN PATENT DOCUMENTS

WO  WO 99/32138  7/1999

OTHER PUBLICATIONS

Callard and Gearing (1994), The Cytokine Factsbook (pp. 97-98).*
Beers & Berkow, The Merck Manual, 17th edition, pp. 986-995, (1999).*
Aguirre et al., "Role of tumor necrosis factor and gamma interferon in acquired resistance to Cryptococcus neoformans in the central nervous system of mice," *Infect. Immun.*, 63, 1725-1731 (1995).
Armitage et al., *Nature*, 357, 80-82 (1992).

Armitage et al., "CD40L: a multi-functional ligand," *Semin. Immunol.*, 5, 401-412 (1993).
Bag, "Fungal pneumonias in transplant recipients," *Curr. Opin. Pulm. Med.*, 9, 193-198 (2003).
Banchereau et al., "The CD40 antigen and its ligand," *Annu. Rev. Immunol.*, 12, 881-922 (1994).
Barchiesi et al., "Posaconazole and amphotericin B combination therapy against Cryptococcus neoformans infection," *Antimicrob. Agents Chemother.*, 48, 3312-3316 (2004).
Beers & Berkow, *The Merck Manual*, $17^{th}$ Edition, 165-177, 986-995 (1999).
Billiau et al., "Immunomodulatory properties of interferon-gamma. An update," *Ann. N.Y. Acad. Sci.*, 856, 22-32 (1998).
Bogdan, "The function of type I Interferons in antimicrobial immunity," *Curr. Opin. Immunol.*, 12, 419-424 (2000).
Caux et al., "Activation of human dendritic cells through CD40 cross-linking," *J. Exp. Med.*, 180, 1263-1272 (1994).
Charlier et al., "Capsule structure changes associated with Cryptococcus neoformans crossing of the blood-brain barrier," *Am. J. Pathol.*, 166, 421-432 (2005).
Chen et al., "The gamma interferon receptor is required for the protective pulmonary inflammatory response to Cryptococcus neoformans," *Infect. Immun.*, 73, 1788-1796 (2005).
Chiller et al., "Effect of granulocyte colony-stimulating factor and granulocyte-macrophage colony-stimulating factor on polymorphonuclear neutrophils, monocytes or monocytes-derived macrophages combined with voriconazole against Cryptococcus neoformans," *Med. Mycol.*, 40, 21-26 (2002).
Chuntharapai et al., *Method on Enzymology*, 288, 15-27 (1997).
Dromer et al., "Protection of mice against experimental cryptococcosis by anti-Cryptococcus neoformans monoclonal antibody," *Infect. Immun.*, 55, 749-752 (1987).
Dullforce et al., "Enhancement of T cell-independent immune responses in vivo by CD40 antibodies," *Nat. Med.*, 4, 88-91 (1998).
French et al., *Nature Medicine*, 5(5), 548-553 (1999).
Francisco et al., *Cancer Research 60*, 3225-3231 (2000).
Funakoshi et al., *Blood*, 83(10), 2787-2794 (1994).
Grewal et al., "CD40 and CD154 in cell-mediated immunity," *Annu. Rev. Immunol.*, 16, 111-135 (1998).

(Continued)

*Primary Examiner*—Prema Mertz
(74) *Attorney, Agent, or Firm*—Leydig, Voit & Mayer, Ltd.

(57) ABSTRACT

The invention provides a method of treating or preventing a pathologic state in a mammal. The method comprises administering to the mammal a promoter of T-cell expansion and an inducer of CD40 stimulation, wherein CD40 is stimulated on cells of the immune system. The promoter of T-cell expansion and inducer of CD40 stimulation are administered in synergistically effective amounts to treat or prevent the pathologic state in the mammal. The invention also provides a method of assessing the effectiveness of treatment of a pathologic state in a mammal, wherein the mammal has been administered a promoter of T-cell expansion and an inducer of CD40 stimulation, wherein CD40 is stimulated on cells of the immune system. The method comprises measuring the level of at least one antibody in a test sample obtained from the mammal, which at least one antibody is specific for an antigen that is known to be associated with the pathologic state, and wherein the level of the at least one antibody is indicative of the effectiveness of treatment of the pathologic state in the mammal.

14 Claims, No Drawings

OTHER PUBLICATIONS

Herring et al., "Induction of Interleukin-12 and gamma Interferon requires tumor necrosis factor alpha for protective T1-cell-mediated immunity to pulmonary Cryptococcus neoformans infection," *Infect. Immun.*, 70, 2959-2964 (2002).

Huffnagle, "Role of cytokines in T cell immunity to a pulmonary Cryptococcus neoformans infection," *Biol. Signals*, 5, 215-222 (1996).

Huffnagle et al., "Afferent phase production of TNF-alpha is required for the development of protective T cell immunity to Cryptococcus neoformans," *J. Immunol.*, 157, 4529-4536 (1996).

Kawakami et al., "NK cells eliminate Cryptococcus neoformans by potentiating the fungicidal activity of macrophages rather than by directly killing them upon stimulation with IL-12 and IL-18," *Microbiol. Immunol.*, 44, 1043-1050 (2000).

Koguchi et al., "Cryptococcal infection and Th1-Th2 cytokine balance," *Int. Rev. Immunol.*, 21, 423-438 (2002).

Kozel et al., Bivalency is required for anticapsular monoclonal antibodies to optimally suppress activation of the alternative complement pathway by the Cryptococcus neoformans capsule, *Infect. Immun.*, 66, 1547-1553 (1998).

Kozel et al., "mAbs to Bacilius anthracis capsular antigen for immunoprotection in antrax and detection of antigenemia," *Proc. Natl. Acad. Sci. U.S.A*, 101, 5042-5047 (2004).

Kumaratilake et al., "The role of T lymphocytes in Immunity to Plasmodium falciparum. Enhancement of neutrophil-mediated parasite killing by lymphotoxin and IFN-gamma: comparisions with tumor necrosis factor effects," *J Immunol.*, 146, 762-767 (1991).

Le Page et al., "Interferon activation and innate immunity," *Rev. Immunogenet.*, 2, 374-386 (2000).

Leinonen et al., "Class-specific antibody response to group B Neisseria meningitidis capsular polysaccharide: use of polylysine precoating in an enzyme-linked immunosorbent assay," *Infect. Immun.*, 38, 1203-1207 (1982).

Levy et al., "Clinical spectrum of X-linked hyper-IgM syndrome," *J. Pediatr.*, 131, 47-54 (1997).

Lutz et al., "Enhancement of antifungal chemotherapy by Interferon-gamma in experimental systemic cryptococcosis," *J. Antimicrob. Chemother.*, 46, 437-442 (2000).

Ma et al., "CD8 T cell-mediated killing of Cryptococcus neoformans requires granulysin and is dependent on CD4 T cells and IL-15," *J. Immunol.*, 169, 5787-5795 (2002).

Mambula et al., "Human neutrophil-mediated nonoxidative antifungal activity against Cryptococcus neoformans," *Infect. Immun.*, 68, 6257-6264 (2004).

Mendiratta et al., *Human Gene Therapy*, 11, 1851-1862 (Sep. 1, 2000).

Mukherjee et al., "Therapeutic efficacy of monoclonal antibodies to Cryptococcus neoformans glucuronoxylomannan alone and in combination with amphotericin," *B. Antimicrob. Agents Chemother.*, 38, 580-587 (1994).

Murphy et al., "Synergistic anti-tumor responses after administration of agonistic antibodies to CD40 and IL-2: coordination of dendritic and CD8+ cell responses," *J. Immunol.*, 170, 2727-2733 (2003).

Pietrella et al., "Disruption of CD40/CD40L interaction influences the course of Cryptococcus neoformans infection," *FEMS Immunol. Med. Microbiol.*, 40, 63-70 (2004).

Ross et al., "Cryptococcal meningitis and sarcoidosis," *Scand. J. Infect. Dis.*, 34, 937-939 (2002).

Sabeti et al., "CD40L association with protection from severe malaria," *Genes Immun.*, 3, 286-291 (2002).

Shoham et al., "The immune response to fungal infections," *Br. J. Haematol.*, 129, 569-582 (2005).

Siddiqui et al., "IFN-gamma at the site of infection determines rate of clearance of infection In cryptococcal meningitis," *J. Immunol.*, 174, 1746-1750 (2005).

Sundstrom et al., "The glucuronoxylomannan of Cryptococcus neoformans serotype A is a type 2 T-cell-independent antigen," *Infect. Immun.*, 60, 4080-4087 (1992).

Uicker et al., "Cytokine and chemokine expression in the central nervous system associated with protective cell-mediated immunity against Cryptococcus neoformans," *Med. Mycol.*, 43, 27-38 (2005).

Van Kooten et al., "Functions of CD40 on B cells, dendritic cells and other cells," *Curr. Opin. Immunol.*, 9, 330-337 (1997).

Van Kooten et al., "Functional role of CD40 and its ligand," *Int. Arch. Allergy Immunol.*, 113, 393-399 (1997).

Vecchiarelli et al., "T lymphocyte and monocyte interaction by CD40/CD40 ligand facilitates a lymphoproliferative response and killing of Cryptococcus neoformans in vitro," *Eur. J. Immunol.*, 30, 1385-1393 (2000).

Von Leoprechting et al., *Cancer Research*, 59, 1287-1294 (Mar. 15, 1999).

Yamauchi et al., "A role for CD40-CD40 ligand interactions in the generation of type 1 cytokine responses in human leprosy," *J. Immunol.*, 165, 1506-1512 (2000).

Ziebold et al., *Arch. Immunol. Ther. Exp.*, 48, 225-233 (2000).

\* cited by examiner

USE OF A PROMOTER OF T-CELL EXPANSION AND AN INDUCER OF CD40 STIMULATION IN THE TREATMENT OR PREVENTION OF A PATHOLOGIC STATE

CROSS-REFERENCE TO RELATED APPLICATIONS

This patent application is a divisional of U.S. patent application Ser. No. 10/226,959, filed Aug. 23, 2002 now U.S. Pat. No. 7,175,838, which claims the benefit of U.S. Provisional Patent Application No. 60/314,342, filed Aug. 23, 2001.

FIELD OF THE INVENTION

This invention pertains to the use of a promoter of T-cell expansion and an inducer of CD40 stimulation in the treatment or prevention of a pathologic state.

BACKGROUND OF THE INVENTION

The immune system is vital in protecting an organism, particularly a mammal, from invasion of harmful agents. Without such protection, it is likely that the organism would be unable to survive unless enclosed in a completely sterile environment. However, simply having a functional immune system does not provide absolute protection from all foreign substances. For example, some viral infections (e.g., HIV), although foreign, normally do not elicit an immune response, nor do tumor cells, which are simply the organism's own cells that have lost control over their proliferation.

An immune response involves two primary responses. One such response is the "humoral response." In this response, mature B lymphocytes leave the bone marrow to circulate in the blood or lymph or to reside in various lymphoid organs. When antigen cross-links membrane-bound antibody molecules on a mature B-cell, some of the bound antigen is internalized by receptor-mediated endocytosis. After processing the antigen, the B-cell presents the resulting antigenic peptides, together with a class II MHC molecule, on its membrane. A $T_H$ cell specific for the presented antigen-MHC complex then binds to the complex, allowing for a CD40 ligand (CD40L) located on the surface of the $T_H$ cell to associate with a CD40 molecule on the surface of a B-cell (i.e., CD40 ligation). This association contributes to the secretion of a number of cytokines (e.g., IL-2, IL-4, IL-5) by the $T_H$ cell. The cytokines then stimulate various stages of B-cell division and differentiation, which leads to the production of a population of both antibody-secreting plasma cells and memory cells.

The other primary immune response is the "cell-mediated response." In this response, cytokines secreted by $T_H$ cells help to activate various T effector cells. For example, after a $T_C$ cell binds to processed antigen associated with class I MHC molecules on the membrane of an altered self-cell (i.e., cells displaying foreign antigen complexed to an MHC molecule), IL-2 secreted by $T_H$ cells stimulates proliferation and differentiation of the $T_C$ cell. This process generates cytotoxic T lymphocytes (CTLs), which not only mediate membrane damage to the altered self-cell leading to cell lysis, but also produce populations of $T_H$ and $T_C$ cells.

As mentioned above, the interaction of CD40 with its ligand (i.e., CD40L) and the functions carried out by cytokines are involved in directing an immune response. CD40, which belongs to the Tumor Necrosis Factor Receptor (TNF-R) family, is a 45-50 kDa glycoprotein of 277 amino acids, with a 193 amino acid extracellular domain composed of four imperfect repeats of about 40 residues, anchored by a superimposable pattern of six cysteines. CD40 was first identified and functionally characterized on B lymphocytes. However, in recent years it has become apparent that CD40 is more widely expressed, including expression on monocytes, dendritic cells, endothelial cells and epithelial cells. Thus, it is now thought that CD40 plays a more general role in immune regulation. CD40L is a polypeptide of 261 amino acids including a 215 amino acid extracellular domain with five cysteines and is a member of the Tumor Necrosis Factor (TNF) family. CD40L is mainly expressed by activated CD4+ T-cells (i.e., $T_H$ cells). Recently, however, CD40L expression on basophils, eosinophils, activated B-cells and blood dendritic cells also has been reported (See, van Kooten et al., Curr. Opin. Immunol. 9: 330-337 (1997)).

Cytokines also play a role in directing an immune response. Most mature CD4+ $T_H$ cells express one of two cytokine profiles: $T_H1$ or $T_H2$. $T_H1$ cells express IL-3, IL-4, IL-5, IL-6, IL-9, IL-10, IL-13, INF-δ, GM-CSF and low levels of TNF-α. The $T_H1$ subset promotes delayed-type hypersensitivity, cell-mediated immunity, and immunoglobulin class switching to IgG2a. The $T_H2$ subset induces humoral immunity by activating B-cells, promoting antibody production, and inducing class switching to IgG1 and IgE.

Since there are many different signals involved in an immune response requiring the interaction of a number of molecules, it is apparent that proper communication between these molecules is necessary for an immune response to occur. A better understanding of this communication will allow for many new prophylactic and therapeutic treatment regimens to be developed for various disease states. For example, it has recently been found that CD40 and various cytokines may play a role in cancer as well as a number of infectious diseases. Indeed, it has been determined that certain cytokines (e.g., IFN-γ, TNF-α, etc.) can up-regulate CD40 expression in some malignant cells that constitutively express CD40. It also has been found that treating certain malignant cells (e.g., melanoma cells) with IFN-γ for 24 hours prior to CD40 stimulation has an additive effect on the release of proinflammatory cytokines by the melanoma cells (see, e.g., Von Leoprechting et al., Cancer Research 59: 1287-1294 (Mar. 15, 1999); and Ziebold et al., Arch. Immunol. Ther. Exp. (Warsz) 48(4): 225-233 (2000)). Additionally, it has been determined that low doses of IL-2 may have a certain level of specific activity in the treatment of cancer, HIV infection and AIDS (see, e.g., U.S. Pat. No. 6,054,788).

While these methods of treatment may provide some relief to cancer, infectious disease and other pathologic states, there is a need for more effective treatments. Indeed, according to the American Cancer Society, the lifetime risk that an individual will develop cancer is 1 in 2 for men and 1 in 3 for women. Moreover, 36.1 million people are currently estimated to be living with HIV/AIDS with an estimated 21.8 million people having died from AIDS since the epidemic began (see, Centers for Disease Control and Prevention, National Center for HIV, STD and TB Prevention). Clearly, a need remains for more effective treatment and preventative measures for these and other pathologic states such that they can be sufficiently treated and controlled.

The present invention provides such a method. These and other advantages of the invention, as well as additional inventive features, will be apparent from the description of the invention provided herein.

BRIEF SUMMARY OF THE INVENTION

The present invention provides a method of treating or preventing a pathologic state in a mammal. The method comprises administering to the mammal a promoter of T-cell expansion and an inducer of CD40 stimulation, wherein CD40 is stimulated on cells of the immune system. The promoter of T-cell expansion and inducer of CD40 stimulation are administered in synergistically effective amounts to treat or prevent the pathologic state in the mammal.

Further provided by the present invention is a method of assessing the effectiveness of treatment of a pathologic state in a mammal, wherein the mammal has been administered a promoter of T-cell expansion and an inducer of CD40 stimulation, wherein CD40 is stimulated on cells of the immune system. The method comprises measuring the level of at least one antibody in a test sample obtained from the mammal, which at least one antibody is specific for an antigen that is known to be associated with the pathologic state, and wherein the level of the at least one antibody is indicative of the effectiveness of treatment of the pathologic state in the mammal.

DETAILED DESCRIPTION OF THE INVENTION

The present invention provides a method of treating or preventing a pathologic state in a mammal comprising administering to the mammal (a) a promoter of T-cell expansion and (b) an inducer of CD40 stimulation, wherein CD40 is stimulated on cells of the immune system, and wherein (a) and (b) are administered in synergistically effective amounts to treat or prevent the pathologic state in the mammal, whereupon the pathologic state in the mammal is treated or prevented. By "preventing" (as used throughout herein) is meant any degree of inhibition of a pathologic state, including infection by a virus, fungus or bacterium, and an allergic condition, up to and including complete inhibition or prevention, wherein, when less than complete inhibition or prevention is realized, at least a beneficial effect is realized The finding is based on the discovery that when a promoter of T-cell expansion is administered to a mammal in combination with an inducer of CD40 stimulation, a synergistic effect on the immune response is achieved. Indeed, the combination is necessary as neither treatment alone has a significant effect when used to treat a mammal for a pathologic state.

The promoter of T-cell expansion used in the context of the present invention can be any suitable promoter of T-cell expansion such that, after administration, the level of T-cells produced is increased over the levels already present in the mammal. Preferably, the promoter of T-cell expansion is a cytokine. The term "cytokine" is used as a generic name for a diverse group of soluble proteins and peptides, which act as humoral regulators either under normal or pathological conditions, and which modulate the functional activities of individual cells and tissues. These proteins also mediate interactions between cells directly and regulate processes taking place in the extracellular environment. Examples of cytokines include, but are not limited to, interleukins, interferons (i.e., INF-α, INF-β, INF-γ), leukemia inhibitory factor (LIF), oncostatin M (OSM), granulocyte-macrophage colony stimulating factor (GM-CSF), granulocyte colony stimulating factor (G-CSF), tumor necrosis factor-alpha (TNF-α), tumor necrosis factor-beta (TNF-β), and transforming growth factor-beta (TGF-β). Preferably, the cytokine is an interleukin and is selected from the group consisting of IL-1, IL-2, IL-3, IL-4, IL-5, IL-6, IL-7, IL-8, IL-9, IL-10, IL-11, IL-12, IL-13, IL-14, IL-15, IL-16, and IL-21. More preferably, the cytokine is an interleukin and is selected from the group consisting of IL-2 and IL-15, and, most preferably, the cytokine is IL-2.

The inducer of CD40 stimulation used in conjunction with the present invention can be any suitable inducer of CD40 stimulation such that CD40 is stimulated on cells of the immune system. Typically, the inducer of CD40 stimulation is a soluble CD40L molecule or an anti-CD40 antibody (e.g., FGK 45). While it is suitable for CD40 to be stimulated on any cell of the immune system where CD40 is normally present (i.e., expressed), CD40 is generally stimulated on antigen presenting cells, such as B-cells, monocytes (e.g., macrophages), and dendritic cells. Preferably, CD40 is stimulated on dendritic cells. Dendritic cells form the link between the innate and the acquired immune system by presenting antigens as well as through their expression of pattern recognition receptors, which detect microbial molecules. Since dendritic cells form the link between the innate and the acquired immune system, the ability to enhance dendritic cell formation with a promoter of T-cell expansion and inducer of CD40 stimulation supports the use of combination based strategies for immunotherapy against a variety of pathologic states. Indeed, the administration of a promoter of T-cell expansion and inducer of CD40 stimulation to a mammal enhances the formation of dendritic cells and allows for the local release of cytokines in the mammal. Specifically, CD40 stimulation induces dendritic cell formation, which in turn release IL-12 locally. The presence of the promoter of T-cell expansion (e.g., IL-2) then allows for T-cells (e.g., $CD8^+$ cells) to expand in response to the dendritic cells. In effect, the promoter of T-cell expansion and inducer of CD40 stimulation work in combination to treat or prevent a pathologic state. Moreover, the local release of cytokines in vivo allows for little-to-no toxicity following treatment as compared to systemic administration of one or more cytokines.

Optionally, an antigen can be administered with the promoter of T-cell expansion and inducer of CD40 stimulation. An "antigen," as used herein, is a molecule capable of provoking an immune response. Antigens can include, for example, cells, cell extracts, polysaccharides, polysaccharide conjugates, lipids, glycolipids, carbohydrates, peptides, proteins, viruses, and viral extracts. Typically, the antigen will be an antigen that is known to be associated with a pathologic state, such as cancer (e.g., a cancer antigen), an infectious disease (e.g., a microbial antigen), or an allergic condition (e.g., an allergen).

The method of the present invention is useful for treating or preventing a pathologic state by stimulating an antigen-specific immune response against a particular antigen. The pathologic state can be characterized as any disease state experienced by a mammal, which can be treated or prevented using the methods of the present invention. For example, the method of the invention is useful for treating or preventing cancer, infectious diseases, and allergic conditions in a mammal. In particular, the method of the invention is useful for treating or preventing cancer in a mammal. A "cancer antigen," as used herein, is a molecule, such as a peptide, associated with a tumor or cancer cell surface and which is capable of provoking an immune response when expressed on the surface of an antigen presenting cell. Cancer antigens include a cancerous cell and immunogenic portions thereof. Typically, the method of the present invention is directed towards cancer antigens located on or within cancers derived from epithelial cells, i.e., are useful for treating or preventing cancers of epithelial origin. Preferably, the cancer is lung cancer (e.g., small cell and non-small cell), such as Lewis lung cancer, or renal cancer. The cancer can be metastatic. Other cancers that can be treated or prevented using the method of the invention can include bile duct cancer; bladder cancer; bone cancer; brain and spinal chord cancers; breast cancer; cervical cancer; lymphoma; colon and rectal cancer; endometrial cancer; esophageal cancer; gallbladder cancer; gastrointestinal cancer; laryngeal cancer; leukemia; liver cancer; multiple myeloma; neuroblastoma; ovarian cancer; pancreatic cancer; prostatic cancer; retinoblastoma; skin cancer (e.g., melanoma and non-melanoma); stomach cancer; testicular cancer; thymus cancer; thyroid cancer; as well as other carcinomas and sarcomas.

The method of the invention is also useful for treating or preventing infectious diseases. An infectious disease, as used herein, is a disease arising from the presence of a foreign microorganism in the body. The promoter of T-cell expansion and inducer of CD40 stimulation are used in combination to stimulate an antigen-specific immune response, which can activate a humoral and/or cell-mediated response against an antigen of the microorganism. The method is accomplished in the same way as described above for cancer, except that the immune response is elicited towards an antigen specific for a microorganism, such as infectious viruses, infectious bacteria, and infectious fungi. Such microbial antigens include the intact microorganism as well as natural isolates and fragments or derivatives thereof and also synthetic compounds, which are identical to or similar to natural microorganism antigens and induce an immune response (humoral and/or cell-mediated) specific for that microorganism. Such antigens are well-known and used routinely in the alt.

Preferably, the infectious disease is a viral or fungal infection, where cell-mediated immune responses are critical. The infectious virus can be any virus known in the art including both RNA and DNA viruses. For example, the virus can belong to the family of Retroviridae (e.g., human immunodeficiency viruses, such as HIV-1); Picornaviridae (e.g., aphthoviruses, cardioviruses, enteroviruses, hepatoviruses, parechoviruses, rhinoviruses); Togaviridae (e.g., alphaviruses, rubiviruses); Rhabdoviridae (e.g., cytorhabdoviruses, ephemeroviruses, lyssaviruses, vesiculoviruses); Filoviridae (e.g., ebola viruses); Paramyxoviridae (e.g., morbilliviruses, paramyxoviruses, rubulaviruses, pneumoviruses); Orthomyxoviridae (e.g., influenza viruses); Arenaviridae (hemorrhagic fever viruses); Reoviridae (e.g., aquareoviruses, orbiviruses, rotaviruses); Bimaviridae; Hepadnaviridae (Hepatitis B virus); Papillomaviridae (papilloma viruses, polyoma viruses); Adenoviridae; Herpesviridae (herpes simplex virus (HSV) 1 and 2, varicelloviruses, cytomegalovirus (CMV), herpes virus); Poxyiridae (variola viruses, vaccinia viruses, pox viruses); Iridoviridae (e.g., iridoviruses, ranaviruses); and unclassified viruses (e.g., the etiological agents of Spongiform encephalopathies; Hepatitis C; Norwalk and related viruses; and astroviruses).

The infectious fungus also can be any fungus known in the art. Examples of infectious fungi can include, for example, *Histoplasma capsulatum, Coccidioides immitis, Blastomyces dermatitidis, Chlamydia trachomatis*, and *Candida albicans*. Other infectious organisms include: *Plasmodium* such as *Plasmodium falciparum, Plasmodium malariae, Plasmodium ovale*, and *Plasmodium vivax* and *Toxoplasma gondii*.

The infectious disease also can be a bacterial infection. Both gram-negative (e.g., *Escherichia coli (E. coli), Pseudomonas* species, and *Salmonella* species) and gram-positive bacteria (e.g., *Pasteurella* species, *Staphylococcus* species, and *Streptococcus* species) can serve as antigens in a mammal. Specific examples of infectious bacteria include, but are not limited to, *Helicobacter pylori, Legionella pneumophila, Staphylococcus aureus, Neisseria gonorrhoea, Neisseria meningitidis, Listeria monocytogenes, Streptococcus pyogenes, Streptococcus faecalis, Streptococcus bovis, Streptococcus pneunmoniae, Haemophilus influenzae, Bacillus anthracis, Corynebacterium diphtheriae, Erysipelothrix rhusiopathiae, Clostridium perfringens, Clostridium tetani, Enterobacter aerogenes, Klebsiella pneunmoniae, Fusobacterium nucleatum, Streptocabillus moniliformis, Treponema palladium*, and *Actinomyces israelii*, as well as various species belonging to the genera of *Mycobacterium, Campylobacter, Enterococcus, Bacteroides*, and *Leptosipira*.

The method of the invention is also useful for treating or preventing allergic conditions. An allergic condition can occur when a mammal acquires hypersensitivity to an allergen. An "allergen" refers to a substance that can induce an allergic response in a susceptible mammal. The allergen is typically an animal or plant allergen such as, for example, pollens, insect venoms, animal dander, dust, and fungal spores, but also can be a food or drug (e.g., penicillin). Allergic conditions include, but are not limited to, eczema, allergic rhinitis or coryza, hay fever, bronchial asthma, urticaria (hives) and food allergies, and other atopic conditions. The method is accomplished in the same way as described above for cancer and infectious disease, except that the immune response is elicited towards an antigen that is specific for an allergen.

Whether the method of the invention is used to treat or prevent a pathologic state in a mammal will depend upon the condition of the pathologic state (e.g., whether or not the mammal has developed the pathologic state). If the pathologic state or other condition associated with the pathologic state is present, the methods of the invention can be used to treat the pathologic state. Alternatively, the mammal may have not yet acquired the pathologic state but may be at risk of developing the pathologic state. A mammal at risk of developing a pathologic state is one who is or who has a high probability of developing the pathologic state. These mammals include, for example, mammals having a genetic abnormality, the presence of which has been demonstrated to have a correlative relation to a higher likelihood of developing a pathologic state, and mammals exposed to harmful agents, such as chemical toxins (e.g., tobacco, asbestos) or radiation. When a mammal at risk of developing a pathologic state is administered a promoter of T-cell expansion and an inducer of CD40 stimulation on a controlled regimen, such as daily, the mammal can recognize and produce an antigen-specific immune response. For example, if a mammal has been administered a promoter of T-cell expansion and an inducer of CD40 stimulation and, over time, a tumor begins to form in the mammal, the immune system of the mammal can respond specifically to one or more of the cancer antigens located on or within the tumor.

The promoter of T-cell expansion and inducer of CD40 stimulation can be administered to the mammal in combination with a targeting means (e.g., a molecule that increases the affinity of the promoter of T-cell expansion and/or inducer of CD40 stimulation for a target cell, such as a dendritic cell). The targeting means can be administered separately or can be associated with (e.g., ionically or covalently bounded to, or encapsulated with) the promoter of T-cell expansion and/or inducer of CD40 stimulation. Examples of a targeting means include, for example, a sterol (e.g., cholesterol), a lipid (e.g., a cationic lipid, virosome or liposome), or a target cell-specific binding agent (e.g., a ligand recognized by target cell specific receptor). Preferred targeting means should be sufficiently stable in vivo to prevent significant uncoupling prior to binding to the target cell. However, the complex should be cleavable under appropriate conditions such that the promoter of T-cell expansion and inducer of CD40 stimulation are released in a functional form. For example, if the targeting means is associated with the promoter of T-cell expansion and the inducer of CD40 stimulation, the targeting means should be cleavable under appropriate conditions such that the promoter of T-cell expansion and inducer of CD40 stimulation are released and allowed to carry out their respective function. More than one targeting means can be used in the context of the invention. In such instances, the promoter of T-cell expansion and the inducer of CD40 stimulation can be attached to the same or different targeting means. In this respect, the promoter of T-cell expansion and the inducer of CD40 stimulation can be targeted to the same or different cells.

The method of the invention can be accomplished using various administration procedures. For example, one contemplated procedure involves isolation of immune system cells (e.g., dendritic cells) from a mammal, manipulation of the cells outside of the body, and reimplantation of the manipulated cells into the mammal. In preferred embodiments, dendritic cells are used and are isolated from peripheral blood or bone marrow, but may be isolated from any source of dendritic cells. When this procedure is performed to produce specifically immune system cells active against a pathologic state, the immune system cells can be exposed to the antigen known to be associated with the pathologic state in addition to the promoter of T-cell expansion and inducer of CD40 stimulation outside of the mammal. In other cases, the immune system cells may have already been exposed to the antigen and are, thus, only exposed to the promoter of T-cell expansion and/or inducer of CD40 stimulation outside of the mammal. Alternatively, the immune system cells can be exposed to the antigen outside the body, and then returned to the body followed by administration of a promoter of T-cell expansion and inducer of CD40 stimulation directly to the mammal, either systemically or locally. Once reimplanted back into the mammal, the activated immune system cells expressing the antigen initiate an immune response specific for the antigen, which response will be enhanced by the promoter of T-cell expansion and inducer of CD40 stimulation. Methods for manipulating immune system cells have been described in several references in the art, including Engleman, Cytotechnology, 25: 1 (1997); Van Schooten et al., Molecular Medicine Today, 255 (June 1997); Steinman, Experimental Hematology, 24: 849 (1996); and Glucknman, Cytokines, Cellular and Molecular Therapy, 3: 187 (1997). Other administration methods involve administering a promoter of T-cell expansion and inducer of CD40 stimulation directly to a mammal in need of therapy, without first isolating immune system cells from the mammal. These agents can be administered in combination with an antigen or can be administered alone. In some embodiments, it is preferred that the promoter of T-cell expansion and inducer of CD40 stimulation be administered in the local region of the pathologic state, which can be accomplished in any way known in the art.

A variety of administration routes are available. The particular mode selected will depend, of course, upon the particular treatment regimen selected, the severity of the pathologic state, and the dosage required for prophylactic or therapeutic efficacy. One skilled in the art will appreciate that suitable methods of administering a promoter of T-cell expansion and an inducer of CD40 stimulation of the invention to a mammal, in particular a human, are available, and, although more than one route can be used to administer a particular agent, a particular route can provide a more immediate and more effective reaction than another route. Accordingly, the herein-described methods are exemplary and are in no way limiting.

The methods of the invention can be practiced using any mode of administration that is medically acceptable, meaning any mode that produces effective levels of the active agents (i.e., antigen, promoter of T-cell expansion, and inducer of CD40 stimulation) without causing clinically unacceptable adverse effects. Such modes of administration include oral, rectal, topical, nasal, interdermal, or parenteral routes. The term "parenteral" includes subcutaneous, intravenous, intramuscular, or infusion. Certain pathologic states (e.g., cancer) are more effective when the mode of administration is at a site on or near the pathologic state.

The promoter of T-cell expansion and inducer of CD40 stimulation can be administered together or separately, in any order, and can be administered by the same or different routes. Whether or not the promoter of T-cell expansion and inducer of CD40 stimulation are administered together or separately or by the same or different route will depend on a variety of factors, including the particular pathologic state involved and the dosage required for prophylactic or therapeutic efficacy. In preferred embodiments, the inducer of CD40 stimulation is administered more often than the promoter of T-cell expansion (e.g., daily vs. every two days). In such instances, the CD40 is administered by itself when the promoter of T-cell expansion is not administered; however, when the promoter of T-cell expansion is also administered, the two agents can be administered together or separately, in any order, and by any suitable route. When the two agents are administered at the same time, it is preferred that the promoter of T-cell expansion and inducer of CD40 stimulation be administered together and by the same route (e.g., parenterally).

The term "synergistically effective amounts" of a promoter of T-cell expansion and inducer of CD40 stimulation refers to the amounts necessary or sufficient to realize a desired biologic effect. For example, synergistically effective amounts of a promoter of T-cell expansion and an inducer of CD40 stimulation for treating or preventing a pathologic state are the amounts necessary to cause activation of the immune system, resulting in the development of an antigen-specific immune response upon exposure to antigen. Synergistically effective amounts, as used herein, are amounts that produce a synergistic immune response against a specific antigen that is greater than the individual effects of either of the promoter of T-cell expansion or the inducer of CD40 stimulation alone.

The synergistically effective amounts for any particular application can vary depending on such factors as the pathologic state being treated; the particular promoter of T-cell expansion or inducer of CD40 stimulation being administered; the size, age, species, and body weight of the mammal; and/or the severity of the pathologic state, and may include one or more of each of the active agents. The synergistically effective amounts will also be determined by the route, timing, and frequency of administration as well as the existence, nature, and extent of any adverse side-effects that might accompany the administration of a particular agent and the desired physiological effect.

The synergistically effective amounts can be determined by conventional range-finding techniques known to those of ordinary skill in the art. Generally, the promoter of T-cell expansion and inducer of CD40 stimulation are initially administered in smaller dosages, which are less than the optimum dose. Thereafter, the dosage is increased by small increments until the optimum effect under the circumstances is reached. The present inventive methods will typically involve the administration of about 0.1-100 mg of one or more of the agents described above per kg body weight.

If an antigen is also administered along with the promoter of T-cell expansion and inducer of CD40 stimulation, it is envisioned that the antigen can be delivered to the mammal using any suitable method known in the art. Such methods include administering the antigen as a nucleic acid or polypeptide molecule. Preferably, the antigen is delivered to the mammal in a nucleic acid molecule, which encodes for the antigen such that the antigen is expressed in vivo. The nucleic acid molecule can also include a sequence encoding a promoter of T-cell expansion and/or a sequence encoding an inducer of CD40 stimulation. The nucleic acid molecule encoding the antigen, promoter of T-cell expansion, and/or inducer of CD40 stimulation is operably linked to a regulatory sequence, which directs the expression of the nucleic acid within a eukaryotic cell. If more than one nucleic acid sequence encoding an active agent is included in the nucleic acid molecule, each sequence can be operably linked to its own regulatory sequence. The "regulatory sequence" is typically a promoter sequence or promoter-enhancer combination, which facilitates the efficient transcription and translation of the nucleic acid to which it is operably linked. The regulatory sequence can, for example, be a mammalian or viral promoter, such as a constitutive or inducible promoter. Exemplary viral promoters which function constitutively in eukaryotic cells include, for example, promoters from the simian virus, papilloma virus, adenovirus, human immunodeficiency virus, Rous sarcoma virus, cytomegalovirus, Moloney leukemia virus and other retroviruses, and Herpes simplex virus. Other constitutive promoters are known to those of ordinary skill in the art. The promoters useful as regulatory sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art and can be used in the context of the invention, when desired. If any active agent is not included in a nucleic acid molecule, that agent can be administered separately using any of the modes of administration described above.

The term "operably linked" as used herein can be defined when a nucleic acid sequence and the regulatory sequence are covalently linked in such a way as to place the expression of the nucleic acid coding sequence under the influence or control of the regulatory sequence. Thus, a regulatory sequence would be operably linked to a nucleic acid sequence if the regulatory sequence were capable of effecting transcription of that nucleic acid sequence such that the resulting transcript is translated into the desired protein or polypeptide.

If a nucleic acid molecule is used, it can be delivered to the immune system alone or in association with a vector. In its broadest sense, a "vector" is any vehicle capable of facilitating the transfer of a nucleic acid to the cells of the immune system, and preferably antigen presenting cells (APCs), so that the antigen can be expressed and presented on the surface of an APC. Moreover, if the promoter of T-cell expansion and inducer of CD40 stimulation are included in the nucleic acid molecule, the vector serves to bring the promoter of T-cell expansion and inducer of CD40 stimulation into close contact with the APC. In general, the vectors useful in the invention include, but are not limited to, plasmids, phagemids, viruses, and other vehicles derived from viral or bacterial sources that have been manipulated by the insertion or incorporation of any nucleic acid sequence of the invention. Preferably, the vector is a viral vector and is selected from the group consisting of an adenovirus, adeno-associated virus, retroviruses, SV40-type viruses, polyoma viruses, Epstein-Barr viruses, papilloma viruses, herpes virus, vaccinia virus, and polio virus.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., *Gene Transfer and Expression, A Laboratory Manual*, W.H. Freeman CO., New York (1990) and Sambrook et al., *Molecular Cloning: A Laboratory Manual*, $2^{nd}$ Ed., Cold Spring Harbor Press, Cold Spring Harbor, N.Y., (1989).

When desirable, the promoter of T-cell expansion and the inducer of CD40 stimulation can be combined prior to administration to form a composition. The composition can comprise additional active ingredients, such as more than one promoter of T-cell expansion and/or more than one inducer of CD40 stimulation.

The compositions conveniently can be presented in unit dosage form and can be prepared by any of the methods well-known in the art. Typically, compositions of the invention are associated with a carrier, which constitutes one or more accessory ingredients. In general, the compositions are prepared by uniformly and intimately bringing the compositions of the invention into association with a liquid carrier, a finely divided solid carrier, or both, and then, if necessary, shaping the product.

The carrier can be any suitable carrier, for example, vehicles, adjuvants, excipients, and diluents. Preferably, the carrier is a pharmaceutically acceptable carrier. With respect to compositions, the carrier can be any of those conventionally used and is limited only by chemico-physical considerations, such as solubility, lack of reactivity with the promoter of T-cell expansion and the inducer of CD40 stimulation, route of administration, and one which has no detrimental side effects or toxicity under conditions of use.

It will be appreciated by one of skill in the art that, in addition to the above-described composition, the compositions of the present invention can be formulated as inclusion complexes, such as cyclodextrin inclusion complexes, or liposomes.

Compositions suitable for oral administration may be presented as discrete units, such as capsules, tablets, lozenges, each containing a predetermined amount of the compositions of the invention. Other compositions include suspensions in aqueous liquids or non-aqueous liquids such as a syrup, elixir or an emulsion.

Other delivery systems can include time-release, delayed release or sustained release delivery systems. Many types of time-release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; peptide based systems; wax coatings; compressed tablets using conventional binders and excipients; partially fused implants; and the like. Specific examples include, but are not limited to: (a) erosional systems in which the compositions of the invention is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term, sustained-release implant can be particularly suitable for treatment of chronic conditions. Long-term release, as used herein, means that the implant is constructed and arranged to deliver therapeutic levels of the active ingredients for at least 30 days, and preferably 60 days. Long-term, sustained-release implants are well-known to those of ordinary skill in the art and include some of the release systems described above.

The method of treating or preventing a pathologic state in a mammal as described herein can be made more effective by administering one or more other compounds along with the promoter of T-cell expansion and inducer of CD40 stimulation. These other compounds are used in accordance with the type of pathologic state they are intended to treat or prevent. For example, when treating cancer, other anticancer compounds can be used in conjunction with the composition of the present invention and include, but are not limited to, all of the known anticancer compounds approved for marketing in the United States and those that will become approved in the future. See, for example, Table 1 and Table 2 of Boyd, *Current Therapy in Oncology*, Section 1. Introduction to Cancer Therapy (J. E. Niederhuber, ed.), Chapter 2, by B.C. Decker, Inc., Philadelphia, 1993, pp. 11-22. More particularly, these other anticancer compounds include doxorubicin, bleomycin, vincristine, vinblastine, VP-16, VW-26, cisplatin, carboplatin, procarbazine, and taxol for solid tumors in general; alkylating agents, such as BCNU, CCNU, methyl-CCNU and DTIC, for brain or kidney cancers; and antimetabolites, such as 5-FU and methotrexate, for colon cancer.

The invention also provides a method of assessing the effectiveness of treatment of a pathologic state in a mammal, wherein the mammal has been administered (a) a promoter of T-cell expansion and (b) an inducer of CD40 stimulation, wherein CD40 is stimulated on cells of the immune system, which method comprises measuring the level of at least one antibody in a test sample obtained from the mammal, which antibody is specific for an antigen that is known to be associated with the pathologic state, and wherein the level of the at least one antibody is indicative of the effectiveness of treatment of the pathologic state in the mammal.

Typically, the test sample used in accordance with the method described herein is taken from the blood or bone marrow of the mammal and will contain a certain level of the at least one antibody. If the test sample is taken from the bone marrow of the mammal, the marrow can be extracted from any bone, however, the pelvic bone is typically used. Methods for extracting immune system cells from blood or bone marrow are well-known in the art and are described in, for example, Citterio et al., Methods 19(1): 142-7 (September 1999). In a preferred embodiment, the effectiveness of treatment of the pathologic state in a mammal is assessed by comparing the level of the at least one antibody in the test sample to the level of at least one antibody in another test sample obtained from the mammal over time, wherein the at least one antibody is the same in both test samples. It will generally be understood that an increase in the level of the at least one antibody over time will be an indication of the treatment being effective in the mammal. Conversely, no change or a decrease in the level of the at least one antibody over time will be an indication of the treatment being ineffective in the mammal. For purposes of the invention, an effective treatment can be defined as any benefit provided to the mammal as a result of the administration of the promoter of T-cell expansion and inducer of CD40 stimulation that increases or is likely to increase the length of survival of the mammal suffering from the pathologic state. An ineffective treatment can be defined in the same way except that there is no increase or no likelihood of an increase in the length of survival of the mammal suffering from the pathologic state. In the event that the mammal has been also administered (c) an antigen that is known to be associated with the pathologic state in addition to the promoter of T-cell expansion and inducer of CD40 stimulation, the at least one antibody that is measured in the test sample will be specific for that antigen. In preferred embodiments, the pathologic state is cancer and the antigen is a cancer antigen.

In general, immunobinding assays can be used to detect, or measure the level of, the at least one antibody in a given test sample. Immunobinding assays involve obtaining a test sample suspected of containing a protein, peptide or antibody corresponding to a particular antigen, and contacting the sample with an antibody in accordance with the present invention, as the case may be, under conditions effective to allow the formation of immunocomplexes. Indeed, the effectiveness of the treatment of the pathologic state in the mammal can be assessed by detecting either an antibody that recognizes the antigen or by quantifying the levels of an antibody that recognizes the antigen.

Any suitable antibody can be used in conjunction with the present invention such that the antibody is specific for the antigen. Additionally, the antibody can recognize other antibodies (i.e., an anti-idiotypic antibody) present in a test sample that bind to the antigen.

The immunobinding assays for use in the present invention include methods for detecting or quantifying the amount of an antigen in a test sample, which methods require the detection or quantitation of any immune complexes formed during the binding process. Here, a test sample suspected of containing an antigen would be obtained from a mammal and subsequently contacted with an antibody. The detection or the quantification of the amount of immune complexes formed under the specific conditions is then performed.

Contacting the test sample with an antibody that recognizes an antigen under conditions effective and for a period of time sufficient to allow formation of immune complexes (primary immune complexes) is generally a matter of simply adding the antibody to the sample and incubating the mixture for a period of time long enough for the antibodies to form immune complexes with, i.e., to bind to, any antigens. After this time, the sample-antibody composition, such as an ELISA plate, dot blot or Western blot, will generally be washed to remove any non-specifically bound antibody species, allowing only those antibodies specifically bound within the primary immune complexes to be detected.

In general, the detection of immunocomplex formation is well-known in the art and can be achieved through the application of numerous approaches. These methods are generally based upon the detection of a label or marker, such as any radioactive, fluorescent, biological or enzymatic tags or labels of standard use in the art. U.S. Patents concerning the use of such labels include U.S. Pat. Nos. 3,817,837, 3,850,752, 3,939,350, 3,996,345, 4,277,437, 4,275,149 and 4,366,241. Of course, additional advantages can be realized by using a secondary binding ligand, such as a second antibody or a biotin/avidin ligand binding arrangement, as is known in the art.

Alternatively, the first added component that becomes bound within the primary immune complexes can be detected by means of a second binding ligand that has binding affinity for the first antibody. In these cases, the second binding ligand is, itself, often an antibody, which can be termed a "secondary" antibody. The primary immune complexes are contacted with the labeled, secondary binding ligand, or antibody, under conditions effective and for a period of time sufficient to allow the formation of secondary immune complexes. The secondary immune complexes are then washed to remove any non-specifically bound labeled secondary antibodies or ligands, and the remaining label in the secondary immune complexes is then detected.

Further methods include the detection of primary immune complexes by a two-step approach. A second binding ligand, such as an antibody, that has binding affinity for the first antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed.

EXAMPLES

The following examples further illustrate the present invention but, of course, should not be construed as in any way limiting its scope.

Example 1

This example demonstrates that a synergistically effective amount of a promoter of T-cell expansion and an inducer of CD40 stimulation can increase the length of survival of mice induced with tumor cells into the kidneys.

Balb/c mice obtained from the Animal Production Area at the National Cancer Institute were injected intrarenally on day 0 with $1 \times 10^5$ Renca cells (Chiron Corporation Emeryville, Calif.). The tumor cells were allowed to grow and tumor-bearing kidneys from these mice were removed on day 11. The mice were then treated from day 12 through day 26 either daily with a phosphate buffer solution (PBS); daily with an inducer of CD40 stimulation (i.e., 100 μg of FGK 45 (Chiron Corporation)); 300,000 IU bid twice per week with a promoter of T-cell expansion (i.e., IL-2 (Chiron Corporation)); or with both of the promoter of T-cell expansion and the inducer of CD40 stimulation using their respective administration regimens above. Surviving mice were rechallenged with $1 \times 10^5$ Renca cells subcutaneously on day 69 and monitored for tumor growth. The mice were monitored daily for their survival. The results of these experiments are summarized in Table 1 below.

TABLE 1

| | Phosphate Buffered Solution (PBS) | FGK 45 | IL-2 | FGK 45 + IL-2 |
|---|---|---|---|---|
| % Survival 0 Days Post Cell Transfer | 100 | 100 | 100 | 100 |
| % Survival 50 Days Post Cell Transfer | 0 | 0 | 0 | 80 |
| % Survival 100 Days Post Cell Transfer | 0 | 0 | 0 | 60 |
| % Survival 150 Days Post Cell Transfer | 0 | 0 | 0 | 60 |

As indicated in Table 1 the survival rate of the mice receiving both the promoter of T-cell expansion and the inducer of CD40 stimulation was significantly higher than the mice receiving no treatment (i.e., PBS) and those mice receiving only the promoter of T-cell expansion or the inducer of CD40 stimulation alone. Moreover, the surviving mice were all subsequently immune to rechallenge of the tumor. These results indicate that the administration of both of a promoter of T-cell expansion and an inducer of CD40 stimulation provides a highly beneficial synergistic effect and is, thus, a potential method of treating a pathologic state, such as renal cancer.

Example 2

This example demonstrates that a synergistically effective amount of a promoter of T-cell expansion and an inducer of CD40 stimulation can increase the length of survival of mice induced with tumor cells into the lungs.

Balb/c mice obtained from the Animal Production Area at the National Cancer Institute were injected intrarenally on day 0 with $1\times10^5$ Lewis lung carcinoma cells. The tumor cells were allowed to grow and tumor-bearing lungs from these mice were removed on day 11. The mice were then treated from day 12 through day 26 either daily with a phosphate buffer solution (PBS), daily with an inducer of CD40 stimulation (i.e., 10 μg of FGK 45 (Chiron Corporation)); 300,000 IU bid twice per week with a promoter of T-cell expansion (i.e., IL-2 (Chiron Corporation)); or with both of the promoter of T-cell expansion and the inducer of CD40 stimulation using their respective administration regimens above. Surviving mice were rechallenged with $1\times10^5$ Lewis lung carcinoma cells subcutaneously on day 69 and monitored for tumor growth. The mice were monitored daily for their survival. The results of the mice surviving after rechallenge of the tumor cells are summarized in Table 2 below.

TABLE 2

| | Phosphate Buffered Solution (PBS) | FGK 45 | IL-2 | FGK 45 + IL-2 |
|---|---|---|---|---|
| % Survival 70 Days Post Cell Transfer | 0 | 31 | 19 | 63 |

As indicated in Table 2, the survival rate of the mice receiving both the promoter of T-cell expansion and the inducer of CD40 stimulation was significantly higher than the mice receiving no treatment (i.e., PBS) and those mice receiving only the promoter of T-cell expansion or the inducer of CD40 stimulation alone after rechallenge of the tumor cells. These results indicate that the administration of both of a promoter of T-cell expansion and an inducer of CD40 stimulation provides a highly beneficial synergistic effect and is, thus, a potential method of treating a pathologic state, such as lung cancer.

Example 3

This example demonstrates that a synergistically effective amount of a promoter of T-cell expansion and an inducer of CD40 stimulation can enhance dendritic cell formation, which, in turn, enhances T-cell formation in a mammal.

Balb/c mice obtained from the Animal Production Area at the National Cancer Institute were treated for 14 days either daily with a phosphate buffer solution (PBS); daily with an inducer of CD40 stimulation (i.e., 100 μg of FGK 45 (Chiron Corporation)); 300,000 IU bid twice per week with a promoter of T-cell expansion (i.e., IL-2 (Chiron Corporation)); or with both of the promoter of T-cell expansion and the inducer of CD40 stimulation using their respective administration regimens above. These mice were sacrificed the day after treatment was stopped (i.e., day 15) and their spleens were removed. Cellularity, total number of $CD8^+$ cells (i.e., Tc cells), and total number of $CD11c/MHC\ II^+$ cells (i.e., dendritic cells) were then measured on a flow cytometer. The results of these experiments are summarized in Table 3 below.

TABLE 3

| | Phosphate Buffered Solution (PBS) | FGK 45 | IL-2 | FGK 45 + IL-2 |
|---|---|---|---|---|
| Cellularity × $10^6$ | 59.2 +/− 27.6 | 122 +/− 38.1 | 102 +/− 28.6 | 157 +/− 56.7 |
| Total $CD8^+$ Cells × $10^6$ | 4.1 +/− 2.4 | 9.5 +/− 4.3 | 6.0 +/− 3.9 | 21.7 +/− 9.6 |
| Total Dendritic Cells × $10^6$ | 8.4 +/− 7.7 | 11.7 +/− 14.3 | 9.6 +/− 9.8 | 34.8 +/− 31.9 |

As indicated in Table 3, total cellularity, total number of $CD8^+$ cells, and total number of dendritic cells were all enhanced in mice receiving both the promoter of T-cell expansion and the inducer of CD40 stimulation as compared to the mice receiving no treatment (i.e., PBS) and those mice receiving only the promoter of T-cell expansion or the inducer of CD40 stimulation alone. These results indicate that the administration of both of a promoter of T-cell expansion and an inducer of CD40 stimulation provides a highly beneficial synergistic effect for increasing cellularity, $CD8^+$ cells, and dendritic cells, which provides for an enhanced immune response.

All of the references cited herein, including patents, patent applications, and publications, are hereby incorporated in their entireties by reference.

While this invention has been described with an emphasis upon preferred embodiments, variations of the preferred embodiments can be used, and it is intended that the invention can be practiced otherwise than as specifically described herein. Accordingly, this invention includes all modifications encompassed within the spirit and scope of the invention as defined by the claims.

What is claimed is:

1. A method of stimulating an immune response against an epithelial cancer in a mammal comprising administering to the mammal (a) interleukin-15 (IL-15) and (b) an inducer of CD40 stimulation that is an anti-CD40 antibody or a soluble CD40 ligand, wherein CD40 is stimulated on cells of the immune system, and wherein (a) and (b) are administered in synergistically effective amounts, whereupon an immune response against the cancer is stimulated in the mammal.

2. The method of claim 1, wherein the inducer of CD40 stimulation is a soluble CD40 ligand.

3. The method of claim 1, wherein the inducer of CD40 is an anti-CD40 antibody.

4. The method of claim 3, wherein the anti-CD40 antibody is FGK 45.

5. The method of claim 1, wherein the epithelial is lung cancer.

6. The method of claim 5, wherein the lung cancer is Lewis lung cancer.

7. The method of claim 1, wherein the epithelial cancer is renal cancer.

8. The method of claim 7, wherein the renal cancer is metastatic.

9. The method of claim 1, wherein the cells of the immune system are antigen presenting cells.

10. The method of claim 9, wherein the cells of the immune system are dendritic cells.

11. The method of claim 1, wherein the administration of (a) and (b) enhances the formation of dendritic cells in the mammal.

12. The method of claim 1, wherein the administration of (a) and (b) allows for the local release of interleukin-12 (IL-12) in the mammal.

13. The method of claim 1, wherein the method further comprises administering (c) a cancer antigen, and the immune response is an antigen-specific immune response against the cancer antigen.

14. The method of claim 1, further comprising administering (c) a molecule that increases the affinity of (a) or (b) for a dendritic cell, wherein the molecule is a sterol, a lipid, or a target cell-specific binding agent.

* * * * *